(12) United States Patent
Clark

(10) Patent No.: US 6,220,097 B1
(45) Date of Patent: Apr. 24, 2001

(54) DEVICE FOR DETECTING DELAMINATIONS AND METHODS OF USE THEREOF

(76) Inventor: Philip Clark, 603 Farmhurst Rd., Baltimore, MD (US) 21208

( * ) Notice: Subject to any disclaimer, the term of this patent is extended or adjusted under 35 U.S.C. 154(b) by 0 days.

(21) Appl. No.: 09/413,812

(22) Filed: Oct. 7, 1999

(51) Int. Cl.[7] .......................... G01M 7/00; G01H 13/00; G01N 33/00
(52) U.S. Cl. ................................. 73/588; 73/866; 73/582
(58) Field of Search ............... 73/866, 588, 582, 73/584

(56) References Cited

U.S. PATENT DOCUMENTS

| | | |
|---|---|---|
| 1,871,756 | 8/1932 | Spath . |
| 2,725,282 | 11/1955 | Buckley et al. ................. 422/82.12 |
| 3,038,320 | 6/1962 | Miller ................................. 73/588 |
| 3,361,225 | 1/1968 | Nichols . |
| 3,714,817 | 2/1973 | Miller . |
| 3,771,354 | 11/1973 | Miller . |
| 3,937,065 | 2/1976 | Milberger et al. . |
| 3,967,498 | 7/1976 | Pezzillo ................................. 73/146 |
| 3,999,626 | 12/1976 | Adams . |
| 4,111,053 | 9/1978 | Geithman et al. ................. 73/588 |
| 4,163,393 | 8/1979 | Gutierrez et al. ................. 73/584 |
| 4,856,334 | 8/1989 | Shearer et al. . |

Primary Examiner—Daniel S. Larkin
Assistant Examiner—Jay L. Politzer
(74) Attorney, Agent, or Firm—Oblon, Spivak, McClelland, Maier & Neustadt, P.C.

(57) ABSTRACT

A device for detecting hidden delaminations in a structure subject to hidden delaminations comprising a rotary percussion tool head adapted at an end thereof to connect to an extension pole, wherein said head comprises at least one circular member, each circular member having on the periphery thereof projections extending in the radial direction and spaced apart in the circumferential direction, and a method of using same.

21 Claims, 2 Drawing Sheets

DEVICE FOR DETECTING DELAMINATIONS AND METHODS OF USE THEREOF

BACKGROUND OF THE INVENTION

1. Field of the Invention

This invention relates to a device for detecting hidden flaws, such as delaminated areas, in a structure such as a concrete slab, and methods of using the device.

2. Discussion of the Background

Methods of and devices for detecting the presence of hidden flaws within steel reinforced suspended concrete slabs have been suggested in the prior art. The flaw to be detected is a separation, or delamination, of the layers of concrete within the slab. The delamination is caused by corrosion of the reinforcing steel within the slab. Corrosion of the steel within the suspended concrete slab is caused when moisture and chlorides make contact with the reinforcing steel. Once the steel begins to corrode, oxidation occurs and the cross-sectional dimension increases which causes areas within the concrete slab to debond and separate into two or more layers. This condition occurs in areas where there are freeze-thaw cycles as well as in areas where there is a preponderance of chlorides, either air-born or where de-icing salts are used for roadways and bridge decks. Once the oxidation and the resultant delamination starts, the rate of deterioration accelerates until a condition exists where large concrete fragments break loose and fall, or, in severe cases, a serious compromise in structural soundness of the slab occurs. Early detection, therefore, of the unseen delamination is important to keep repair costs to a minimum.

In the past, detection of delaminations in the bottom exposed surface of a suspended concrete slab, or soffit, has been to repeatedly tap the surface, usually with a hand held hammer producing the sound which has been found to occur when the slab is delaminated. This method of initially detecting the presence of delamination is regarded as a reliable means to find problem areas which are not visually apparent. Most soffits are out of reach, so a ladder or scaffolding is usually required to reach the surface.

The prior art has employed measurement of sound or vibration variables in order to ascertain changes in a mechanical element, such as a bridge, such as disclosed in U.S. Pat. No. 1,871,756 to Späth. Other prior art references have disclosed various rotary devices for obtaining acoustical data in the inspection of structures, workpieces, etc. for hidden defects, such as U.S. Pat. No. 3,714,817 and U.S. Pat. No. 3,771,354, both to Miller, and U.S. Pat. No. 4,856,334 to Shearer et al. U.S. Pat. No. 3,999,626 to Adams discloses a seismic method and apparatus for generating seismic signals which can be detected at great distances either on the surface or underground. None of the above references are concerned with defects in concrete structures, and all are drawn to relatively complex apparatus.

A method and device in the prior art disclosed for detecting delaminations is the relatively complex apparatus disclosed in U.S. Pat. No. 3,937,065 to Milberger et al. The Milberger et al apparatus is drawn to detecting delaminations beneath a surface and involves the receiving and measuring of acoustical responses with an acoustic receiving transducer, and other sophisticated components. Milberger et al's apparatus is not well adapted for detecting delaminations in areas other than the underside of floors and decks.

Another prior art delamination device is that disclosed in U.S. Pat. No. 3,361,225 to Nichols. Nichols' device comprises in combination an externally-toothed wheel, and means comprising a hand-held handle and means for pivotally mounting the wheel on the handle, for walking the wheel across a member to be tested, for causing the individual teeth of the wheel to sequentially strike the member, for producing individual sequential acoustical sounds indicative of the internal structure of the member, an abnormal acoustical sound being indicative of an abnormal internal structure. As an externally-toothed wheel, Nichols employs a disk and a single substantially coplanar set of radially outwardly-extending pegs mounted on the periphery of the disk. For extremely large panels, Nichols discloses ganging a plurality of such devices, whereby the ganged test devices may be simultaneously rolled across a panel to be tested, wherein each device detects independently of the other. Nichols discloses further the use of an electrical pickup device, such as a microphone, to detect the acoustical sounds in lieu of the use of the human ear and human judgment. The only environment disclosed for use of the Nichols' device, however, is in the detecting of abnormalities in structural elements known as honeycomb panels. A honeycomb panel is defined therein as a three-part sandwich, wherein a central core section is sandwiched between a top and bottom sheet or skin portion. The Nichols' device is intended to detect abnormalities in the bonding of the core to either the top or bottom portion. Nichols suggests nothing with regard to other structures, such as suspended concrete slabs or soffits and other generally inaccessible areas subject to delaminations.

A need thus still exists in the art for a relatively simple and inexpensive device for measuring delaminations in structures subject to such delaminations, and particularly such structures, such as suspended concrete slabs or soffits, that have previously not been tested for delaminations without great effort.

SUMMARY OF THE INVENTION

It is therefore an object of the present invention to provide an improved device which is simple and inexpensive for detecting delaminations in structures subject to such delaminations that heretofore were not easily subject to detection, such as suspended concrete slabs or soffits.

It is another object of the present invention to provide a method for using such a device.

The device is a rotary percussion tool head adapted at an end thereof to connect to an extension pole of any length, thus allowing contact of the tool head with a surface to be detected located at various distances from the testing location, such as the ground.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The device is a rotary percussion tool head adapted at an end thereof to receive an extension pole of any length, thus allowing contact of the tool head with a surface to be detected located at various distances from the testing location, such as the ground.

The preferred use of the device is to conduct sounding analysis to determine the extent of delaminated and spalled concrete in the under side of overhead slabs or soffits. The design of the tool includes a preferably telescopic extension pole and a preferably machined tool head, which allows the work to be done from the slab below, excluding the need for ladders in most applications. The tool-head can be removed and hand held for close work. This significantly speeds the entire process and with considerably less fatigue, while the traditional process of using a hammer is tedious and time consuming.

The tool head comprises at least one, and preferably two, circular members, such as wheels or discs, of equal size and generally parallel to each other, each circular member having on the periphery thereof projections, preferably coplanar, extending in the radial direction and spaced apart, preferably equidistantly, in the circumferential direction. Preferably, each circular member-projections combination is a ball bearing idler sprocket, preferably made out of hardened steel, press-fit mounted and spaced apart from each other to cover an area, preferably about 5 inches, wide. Preferably, the tool head is snap-fit on a telescopic extension pole long enough to reach the exposed surface of the under side or soffit of a suspended steel reinforced concrete slab.

In use, the tool head is rolled along the surface so that the projections each contact the surface sequentially to produce the percussive force to effect the sound necessary to distinguish solid concrete from delaminated or spalled concrete.

The device and method relies on detection by the human ear, as each projection strikes the surface, and the differences in sound between flawed sections and unflawed sections, which are known to persons skilled in the art of detecting delaminations, are easily determined by the human ear alone, and do not need the addition of any acoustical or other enhancements, such as those of Milberger et al or Nichols, supra. While such enhancements are not necessary, the device may contain such enhancements, such as the microphone of Nichols.

Figure 1:
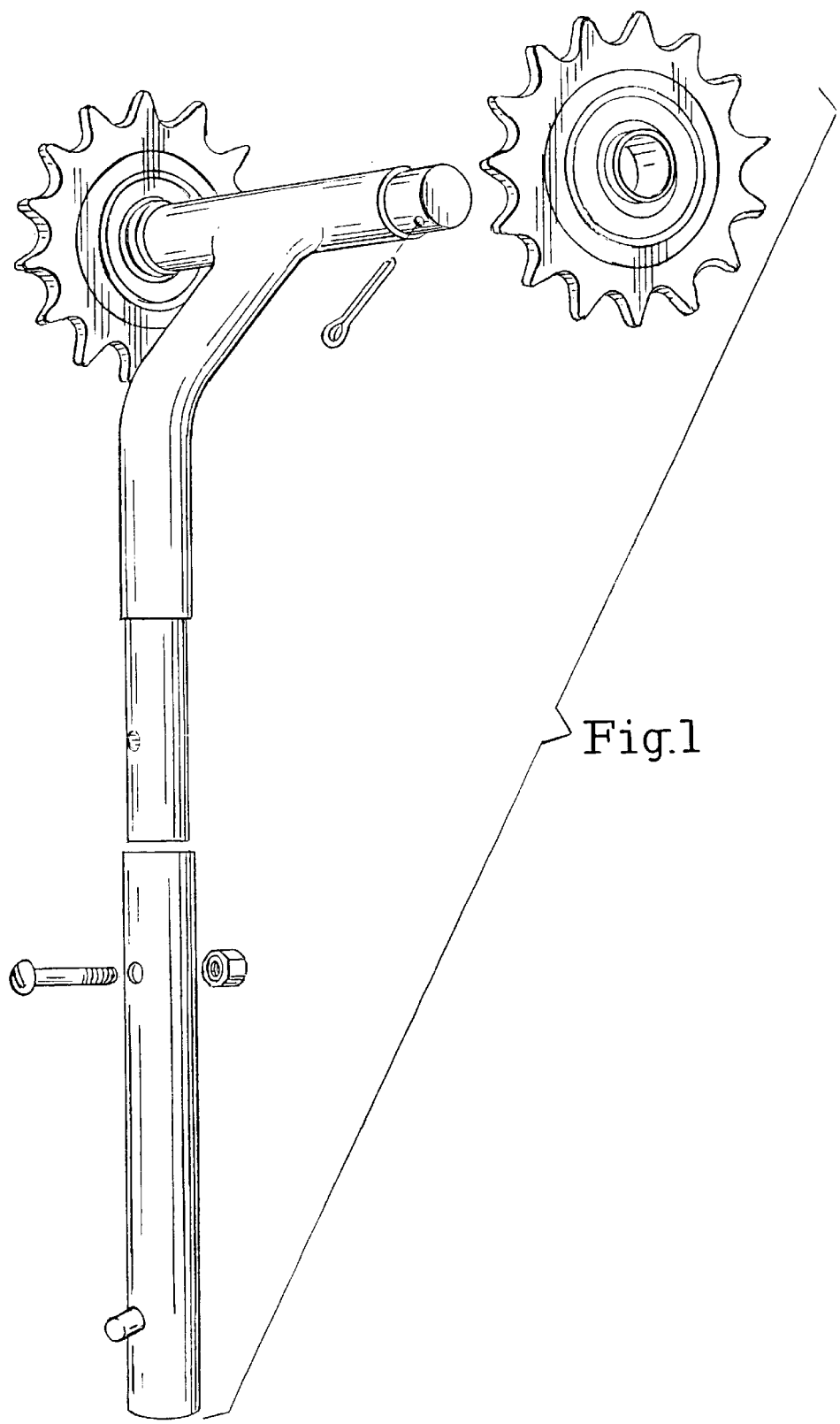
FIG. 1 represents a preferred embodiment of the device.

In a most preferred embodiment, as shown in FIG. 1, the device comprises a "T" shaped chassis with a 45° angle in a plane generally parallel to the plane of each of the sprockets. The material used is round aluminum rod at a diameter of 0.75 inches. One inch on each side of the top portion of the chassis is machined down to a smaller diameter of 0.640 inches to allow the ball bearing idler sprocket to slip onto the chassis and stop against the shoulder of the chassis where the outside diameter is greater. The machined ends of the chassis where the sprockets fit must be machined to a tolerance tight enough to engage the ball bearing and still allow the sprocket to spin. This is referred to as a press-fit bearing. The chassis is angled at 45° to allow easy contact with the surface of the soffit slab. Early prototypes of the tool, which did not have the angle, and thus represents a less preferred embodiment of the present invention, proved to be difficult to maintain constant contact with the surface due to the angle at which the extension pole must be held. That is, the more vertical the extension pole must be held (because the soffit is higher), the more difficult it becomes to maintain constant force. With the angle, however, the tool head is offset and can be rolled along the surface while applying minimum upward force.

At the outside end of the tool chassis, the 0.75 inch round aluminum rod is machined down to 0.640 inch to allow the attachment of an aluminum hollow-tube adapter. This adapter then snaps into a telescopic extension pole to allow a reach of on the order of 12 feet.

Figure 2:
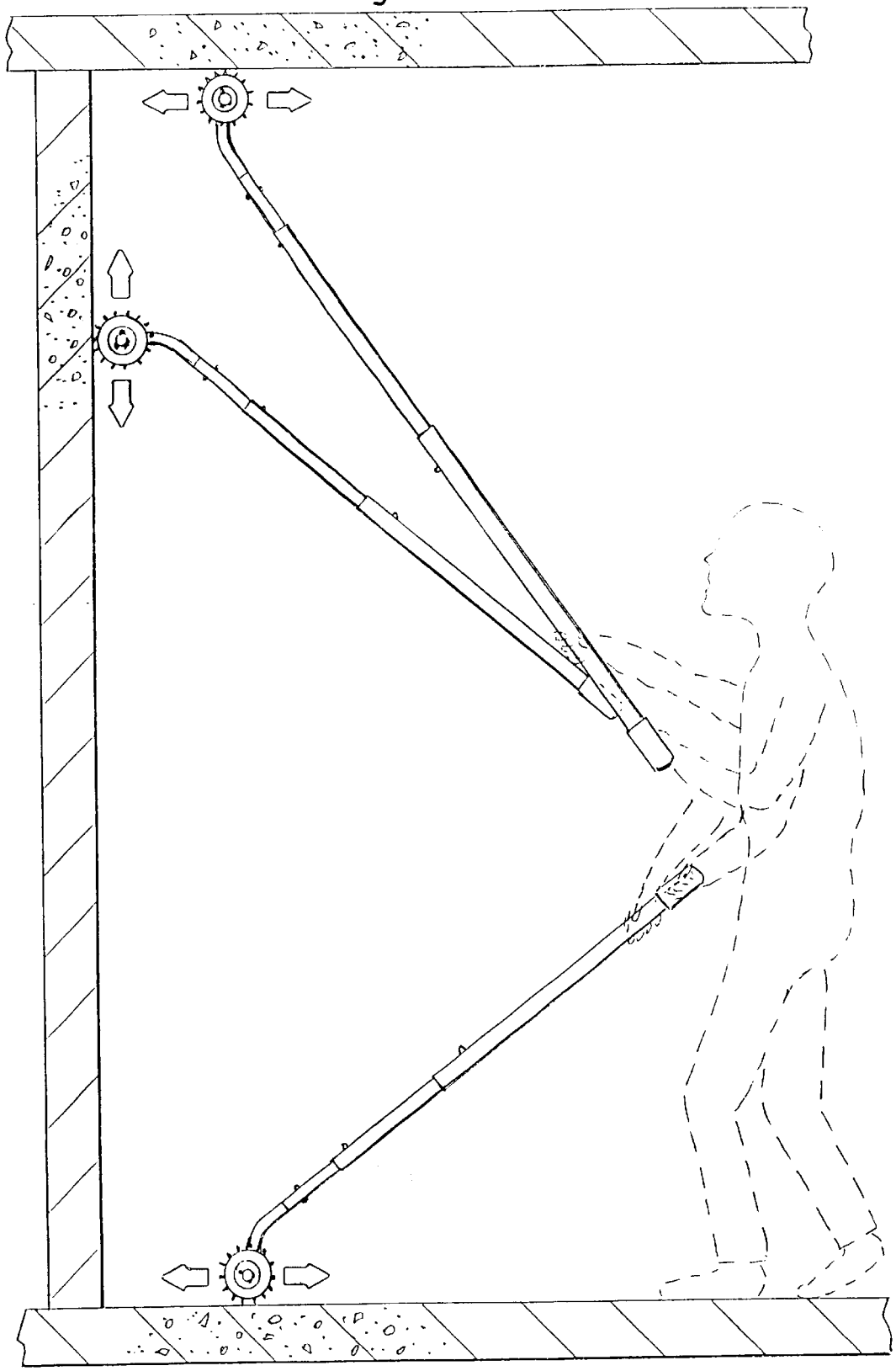
FIG. 2 demonstrates a method of using the device.

FIG. 2 shows a method of using the device on various surfaces, e.g., the ground, a wall, and a soffit.

Materials other than aluminum can be used for the device, including other metals or non-metal natural materials such as wood, or synthetic materials such as plastics. Other angles can be used, depending upon relative locations of tester and surface to be tested. The device can also be made smaller or larger, with concomitant change in rod and pole diameters, depending on the size of the areas to be tested. When more than one circular member is present, the distance between respective members can be set at any distance. While FIG. 1 shows a preferred telescopic extension pole, the present device includes all other means for extending the length of a device, such as smaller sections which can be piggy-backed to each other by connections well-known in the art, such as threaded or press-fitted connections and the like. Additionally, the tool head and any extensions can be fashioned as a unitary article, i.e., wherein the tool head and extensions are constructed as one piece.

Having generally described this invention, a further understanding can be obtained by reference to certain specific examples which are provided herein for purposes of illustration only and are not intended to be limiting unless otherwise specified.

EXAMPLE 1

Field Test Results

The field tests were conducted on concrete structures in the Northeastern U.S. During a typical building evaluation in Washington, D.C., the device shown in FIG. 1 was used to test the extent of delaminated concrete in the soffit slab of a 20,000 square foot parking garage. The evaluation found 1.36% delamination and was completed within 1 hour. Manually, the same process took 5 hours and found only 1.09% delamination. Using the device increased work productivity by 500%. In addition to the significant test results, it became evident that it is equally effective for use on beams, columns and floor slabs. In a parking garage in Baltimore, Md., two beams at a height of 11 feet were analyzed and found to have extensive delaminated concrete on the under side of the beam and on both vertical surfaces. All work was completed without the need for ladders.

Obviously, numerous modifications and variations of the present invention are possible in light of the above teachings. It is therefore to be understood that within the scope of the appended claims, the invention may be practiced otherwise than as specifically described herein.

What is claimed is:

1. A device for detecting hidden delaminations in a structure subject to hidden delaminations comprising a rotary percussion tool head adapted at an end thereof to connect to an extension pole, wherein said head comprises at least one circular member, each circular member having on the periphery thereof projections extending in the radial direction and spaced apart in the circumferential direction wherein the at least one circular member is a hardened steel ball bearing idler sprocket press-fit mounted.

2. The device according to claim 1, wherein said tool head comprises two circular members of equal size and generally parallel to each other.

3. The device according to claim 2, wherein the two circular members are spaced apart.

4. The device according to claim 3, wherein the tool head comprises a "T" shaped chassis.

5. The device according to claim 4, wherein the "T" shaped chassis is bent at an angle in a plane generally parallel to the plane of each of said sprockets.

6. The device according to claim 5, wherein said angle is about 45°.

7. The device according to claim 6, wherein the sprockets are spaced apart to cover an area about 5 inches wide.

8. The device according to claim 1, connected to an extension pole at said end thereof.

9. The device according to claim 2, connected to an extension pole at said end thereof.

10. The device according to claim 3, connected to an extension pole at said end thereof.

11. The device according to claim 4, connected to an extension pole at said end thereof.

12. The device according to claim 5, connected to an extension pole at said end thereof.

13. The device according to claim 6, connected to an extension pole at said end thereof.

14. The device according to claim 7, connected to an extension pole at said end thereof.

15. A method of detecting hidden delaminations above a concrete soffit comprising manually rolling the device of claim 8 on a surface of said soffit such that said projections contact said surface sequentially, and listening to the sound made upon the contact between each projection and said surface.

16. A method of detecting hidden delaminations above a concrete soffit comprising manually rolling the device of claim 9 on a surface of said soffit such that said projections contact said surface sequentially, and listening to the sound made upon the contact between each projection and said surface.

17. A method of detecting hidden delaminations above a concrete soffit comprising manually rolling the device of claim 10 on a surface of said soffit such that said projections contact said surface sequentially, and listening to the sound made upon the contact between each projection and said surface.

18. A method of detecting hidden delaminations above a concrete soffit comprising manually rolling the device of claim 11 on a surface of said soffit such that said projections contact said surface sequentially, and listening to the sound made upon the contact between each projection and said surface.

19. A method of detecting hidden delaminations above a concrete soffit comprising manually rolling the device of claim 12 on a surface of said soffit such that said projections contact said surface sequentially, and listening to the sound made upon the contact between each projection and said surface.

20. A method of detecting hidden delaminations above a concrete soffit comprising manually rolling the device of claim 13 on a surface of said soffit such that said projections contact said surface sequentially, and listening to the sound made upon the contact between each projection and said surface.

21. A method of detecting hidden delaminations above a concrete soffit comprising manually rolling the device of claim 14 on a surface of said soffit such that said projections contact said surface sequentially, and listening to the sound made upon the contact between each projection and said surface.

\* \* \* \* \*